(12) United States Patent
Danielsen et al.

(10) Patent No.: US 6,506,585 B2
(45) Date of Patent: Jan. 14, 2003

(54) POLYPEPTIDES HAVING HALOPEROXIDASE ACTIVITY

(75) Inventors: Steffen Danielsen, Copenhagen (DK); Palle Schneider, Ballerup (DK)

(73) Assignee: Novozymes, A/S, Bagsvaerd (DK)

( * ) Notice: Subject to any disclaimer, the term of this patent is extended or adjusted under 35 U.S.C. 154(b) by 51 days.

(21) Appl. No.: 09/832,441

(22) Filed: Apr. 11, 2001

(65) Prior Publication Data

US 2002/0009434 A1 Jan. 24, 2002

Related U.S. Application Data

(60) Provisional application No. 60/201,090, filed on May 2, 2000.

(30) Foreign Application Priority Data

Apr. 14, 2000 (DK) ......................................... 2000 00625

(51) Int. Cl.[7] ............................. C12N 9/08; C12N 1/20; C12N 15/00; C07K 1/00; C07H 21/04

(52) U.S. Cl. ................. 435/192; 435/252.3; 435/320.1; 435/911; 530/350; 536/23.2

(58) Field of Search ............................. 435/192, 252.3, 435/320.1, 911; 530/350; 536/23.2

(56) References Cited

FOREIGN PATENT DOCUMENTS

| WO | WO 95/27046 | 10/1995 |
|----|-------------|---------|
| WO | WO 97/04102 | 2/1997 |

OTHER PUBLICATIONS

Abstract: Caplus accession No. 1995: 714623; document No. 123:137262.
Simons et al., Eur. J. Biochem. 229, 566–574 (1995).
Schijndel et al., Biochimica et Biophysica Acta 1161 (1993) 249–256.

Primary Examiner—Tekchand Saidha
(74) Attorney, Agent, or Firm—Elias J. Lambiris

(57) ABSTRACT

The present invention relates to isolated polypeptides having haloperoxidase activity. The invention also relates to methods for producing and using the polypeptides

11 Claims, No Drawings

POLYPEPTIDES HAVING HALOPEROXIDASE ACTIVITY

CROSS-REFERENCE TO RELATED APPLICATIONS

This application claims, under 35 U.S.C. 119, priority from or the benefit of Danish application no. PA 2000 00625 filed Apr. 14, 2000, and U.S. application Ser. No. 60/201,090 filed May 2, 2000, the contents of which are fully incorporated herein by reference.

FIELD OF THE INVENTION

The present invention relates to isolated polypeptides having haloperoxidase activity as well as methods for producing and using the polypeptides.

BACKGROUND

Haloperoxidases are widespread in nature being produced by mammals, plants, algae, lichen, bacteria, and fungi. Haloperoxidases are probably the enzymes responsible for the formation of naturally occurring halogenated compounds. There are three types of haloperoxidases, classified according to their specificity for halide ions: Chloroperoxidases (E.C. 1.11.1.10) which catalyze the chlorination, bromination and iodination of compounds; bromoperoxidases which show specificity for bromide and iodide ions; and iodoperoxidases (E.C. 1.11.1.8) which solely catalyze the oxidation of iodide ions.

The first discovered haloperoxidases were determined to contain heme as a prosthetic group or co-factor. However, more recently, it has become apparent that there are numerous non-heme haloperoxidases as well. Bacterial haloperoxidases have been found with no prosthetic group. In addition, a number of other non-heme haloperoxidases have been shown to possess a vanadium prosthetic group. Haloperoxidases containing a vanadium prosthetic group are known to include at least two types of fungal chloroperoxidases from *Curvularia inaequalis* (van Schijndel et al., 1993, *Biochimica Biophysica Acta* 1161:249–256; Simons et al., 1995, *European Journal of Biochemistry* 229: 566–574; WO 95/27046) and *Curvularia verruculosa* (WO 97/04102).

Haloperoxidases, like other oxidoreductases, are of current interest because of their broad range of potential industrial uses.

It is an object of the present invention to provide improved polypeptides having haloperoxidase activity and nucleic acid encoding the polypeptides.

SUMMARY OF THE INVENTION

The present invention relates to isolated polypeptides having haloperoxidase activity selected from the group consisting of:

(a) a polypeptide having an amino acid sequence which has at least 91% homology with the amino acid sequence of SEQ ID NO:2;

(b) a polypeptide encoded by a nucleic acid sequence which hybridizes under medium stringency conditions with (i) the nucleotide sequence of SEQ ID NO:1, (ii) a subsequence of (i) of at least 100 nucleotides, or (iii) a complementary strand of (i) or (ii);

(c) a variant of the polypeptide having an amino acid sequence of SEQ ID NO:2 comprising a substitution, deletion, and/or insertion of one or more amino acids;

(d) an allelic variant of (a) or (b);

(e) a fragment of (a), (b), or (d) that has haloperoxidase activity; and (f) a polypeptide having more than 50% residual activity after 15 minutes incubation at 70° C. and pH 7.

The present invention also relates to methods for producing and using the polypeptides.

DETAILED DESCRIPTION OF THE INVENTION

Polypeptides Having Haloperoxidase Activity

The term "haloperoxidase activity" as defined herein catalyzes the oxidation of a halide ion (X=Cl—, Br—, or I—) in the presence of hydrogen peroxide ($H_2O_2$) to the corresponding hypohalous acid (HOX):

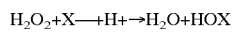

$$H_2O_2 + X^- + H^+ \rightarrow H_2O + HOX$$

For purposes of the present invention, haloperoxidase activity is determined according to the procedure described in "Haloperoxidase assays" in the Examples.

In a first embodiment, the present invention relates to isolated polypeptides having an amino acid sequence which has a degree of homology to the amino acid sequence of SEQ ID NO:2 of at least about 91%, preferably at least about 95%, and more preferably at least about 97%, which have haloperoxidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of homology between two amino acid sequences is determined by using GAP version 8 from the GCG package (Genetics Computer Group, 575 Science Drive, Madison, Wis. 53711, USA) with standard penalties for proteins: GAP weight 3.00, length weight 0.100, Matrix described in Gribskov and Burgess, Nucl. Acids Res. 14(16); 6745–006763 (1986).

Preferably, the polypeptides of the present invention comprise the amino acid sequence of SEQ ID NO:2 or an allelic variant thereof; or a fragment thereof that has haloperoxidase activity. In a more preferred embodiment, the polypeptide of the present invention comprises the amino acid sequence of SEQ ID NO:2. In another preferred embodiment, the polypeptide of the present invention consists of the amino acid sequence of SEQ ID NO:2 or an allelic variant thereof; or a fragment thereof that has haloperoxidase activity. In another preferred embodiment, the polypeptide of the present invention consists of the amino acid sequence of SEQ ID NO:2.

A fragment of SEQ ID NO:2 is a polypeptide having one or more amino acids deleted from the amino and/or carboxyl terminus of this amino acid sequence.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having haloperoxidase activity which are encoded by nucleic acid sequences which hybridize under medium stringency conditions, preferably medium-high stringency conditions, more preferably high stringency conditions, and most preferably very high stringency conditions with a nucleic acid probe which hybridizes under the same conditions with (i) the nucleotide sequence of SEQ ID NO:1, (ii) a subsequence of (i), or (iii) a complementary strand of (i) or (ii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment, which has haloperoxidase activity. The polypeptides may also be allelic variants or fragments of the polypeptides that have haloperoxidase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having haloperoxidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA, which hybridizes with the probes described above and which encodes a polypeptide having haloperoxidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the nucleic acid sequence contained in the pUC19 derived plasmid contained in *Escherichia coli* DH10B, deposited as DSM 13441, wherein the nucleic acid sequence encodes a polypeptide having haloperoxidase activity.

For long probes of at least 100 nucleotides in length, low to very high stringency conditions are defined as prehybridization and hybridization at 42°C. in 5× SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2× SSC, 0.2% SDS preferably at least at 50°C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6× SSC plus 0.1% SDS for 15 minutes and twice each for 15 minutes using 6× SSC at 5° C. to 10° C. below the calculated $T_m$.

In a third embodiment, the present invention relates to variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions, which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having a residual activity of at least 40% after 15 minutes incubation at 80° C. and pH 7. In a preferred embodiment, the polypeptides of the invention retain at least 50% residual activity, preferably at least 70% residual activity after 15 minutes incubation at 70° C. and pH 7. In another preferred embodiment, the polypeptides of the invention retain at least 50% residual activity, preferably at least 85% residual activity after 15 minutes incubation at 60° C. and pH 7.

In a preferred embodiment, the polypeptides of the invention contain a vanadium prosthetic group, and accordingly they are vanadium haloperoxidases. In another preferred embodiment, the polypeptides of the invention are chloroperoxidases.

In a fifth embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide, which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide, which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the haloperoxidase activity of the polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In a preferred embodiment, the polypeptide is a *Phaeotrichoconis crotalariae* polypeptide, more preferably a *Phaeotrichoconis crotalariae* haloperoxidase, and most preferably a *Phaeotrichoconis crotalariae* haloperoxidase encoded by the nucleic acid sequence contained in the plasmid contained in *E. coli* DH10B, deposited as DSM 13441, e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-haloperoxidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences, which encode a polypeptide of the present invention. In a preferred embodiment, the nucleic acid sequence is set forth in SEQ ID NO:1. In another more preferred embodiment, the nucleic acid sequence is the sequence contained in the pUC19 derived plasmid contained in *Escherichia coli* DH10B, deposited as DSM 13441. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 that have haloperoxidase activity.

A subsequence of SEQ ID NO:1 is a nucleic acid sequence encompassed by SEQ ID NO:1 except that one or more nucleotides from the 5' and/or 3' end have been deleted.

The present invention also relates to mutant nucleic acid sequences comprising at least one mutation in the polypeptide coding sequence of SEQ ID NO:1, in which the mutant nucleic acid sequence encodes a polypeptide which consists of the amino acid sequence of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Phaeotrichoconis, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the polypeptide coding sequence of SEQ ID NO:1 of at least about 86%, preferably about 90%, more preferably about 95%, and most preferably about 97% homology, which encode an active polypeptide. For purposes of the present invention, the degree of homology between two nucleic acid sequences is determined by using GAP version 8 from the GCG package with standard penalties for DNA: GAP weight 5.00, length weight 0.300, Matrix described in Gribskov and Burgess, Nucl. Acids Res. 14(16); 6745–6763 (1986).

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for haloperoxidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under low stringency conditions, preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under low, medium, medium-high, high, or very high stringency conditions with (i) the nucleotide sequence of SEQ ID NO:1, (ii) a subsequence of (i), or (iii) a complementary strand of (i), (ii) or (iii); and (b) isolating the nucleic acid sequence. The subsequence is preferably a sequence of at least 100 nucleotides such as a sequence, which encodes a polypeptide fragment which has haloperoxidase activity.

Methods for Producing Mutant Nucleic Acid Sequences

The present invention further relates to methods for producing a mutant nucleic acid sequence, comprising introducing at least one mutation into the polypeptide coding sequence of SEQ ID NO:1 or a subsequence thereof, wherein the mutant nucleic acid sequence encodes a polypeptide which consists of the amino acid sequence of SEQ ID NO:2 or a fragment thereof which has haloperoxidase activity.

The introduction of a mutation into the nucleic acid sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences, which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence, which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components, which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5′-phosphate decarboxylase), sC (sulfate adenyltransferase), and trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* and *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carisbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a Fusarium venenatum (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Phaeotrichoconis, and more preferably *Phaeotrichoconis crotalariae*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the polypeptide coding region of SEQ ID NO:1, wherein the mutant nucleic acid sequence encodes a polypeptide which consists of the amino acid sequence of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell, which has been transformed with a nucleic acid sequence encoding a polypeptide having haloperoxidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct, which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S—CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron, which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto etal., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having haloperoxidase activity of the present invention under conditions conducive for production of the polypeptide; and (b) recovering the polypeptide.

Compositions

In a still further aspect, the present invention relates to compositions comprising a polypeptide of the present invention. Preferably, the compositions are enriched in a polypeptide of the present invention. In the present context, the term "enriched" indicates that the haloperoxidase activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus*, *Aspergillus awamori*, *Aspergillus niger*, or *Aspergillus olyzae*, or Trichoderma, Humicola, preferably *Humicola insolens*, or Fusarium, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Composition

The haloperoxidase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the haloperoxidase of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167,170, 194, 206, 218, 222, 224,235 and 274.

Preferred commercially available protease enzymes include Alcalase™, Savinase™, Primase™, Everlase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases:

Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *P. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases:

Suitable amylases (α and/or β) include those of bacterial or fungal origin. Chemically modified or protein engineered mutants are included. Amylases include, for example, α-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188,190, 197,202,208, 209, 243,264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the haloperoxidase of the invention, may be added in an amount corresponding to 0.01–100 mg of enzyme protein per liter of wash liqour, preferably 0.05–5 mg of enzyme protein per liter of wash liquor, in particular 0.1–1 mg of enzyme protein per liter of wash liquor.

The haloperoxidase of the invention may additionally be incorporated in the detergent formulations disclosed in WO 97/07202, which is hereby incorporated as reference.

Uses

The present invention is also directed to methods for using the polypeptides having haloperoxidase activity.

The present invention is further directed to methods of oxidizing a halide ion to the corresponding hypohalous acid, comprising reacting the halide ion and a source of hydrogen peroxide in the presence of a haloperoxidase of the invention. The present invention also relates to methods of halogenating a compound comprising reacting the compound, a halide ion and a source of hydrogen peroxide in the presence of a haloperoxidase of the invention.

The present invention also relates to methods for killing or inhibiting the growth of microbial cells, comprising contacting the cells with a haloperoxidase of the invention, a source of hydrogen peroxide, and a source of halide or thiocyanate in an aqueous solution.

The source of hydrogen peroxide can be hydrogen peroxide itself or a hydrogen peroxide precursor, such as, a percarbonate, perborate, peroxycarboxylic acid or a salt thereof. Furthermore, the source may be a hydrogen peroxide generating enzyme system, such as an oxidase, e.g., a glucose oxidase, glycerol oxidase or amino acid oxidase, and its substrate. The hydrogen peroxide source may be added in a concentration corresponding to a hydrogen peroxide concentration in the range of from about 0.001 to about 10 mM, preferably about 0.01 to about 1 mM.

The halide source may be a halide salt, preferably a sodium or potassium salt, such as sodium chloride, potassium chloride, sodium bromide, potassium bromide, sodium iodide, or potassium iodide. The thiocyanate source may be a thiocyanate salt, preferably a sodium or potassium salt.

The concentration of the halide source will typically correspond to 0.001–1000 mM, preferably in the range of from 0.005–500 mM, more preferably in the range of from 0.01–100 mM, and most preferably in the range of from 0.05–50 mM.

The haloperoxidases may be used as preservation agents and disinfection agents such as in water based paints and personal care products, e.g., toothpaste, mouthwash, skin care creams and lotions, hair care and body care formulations, solutions for cleaning contact lenses and dentures. The haloperoxidases also may be used for cleaning surfaces and cooking utensils in food processing plants and in any area in which food is prepared or served. The haloperoxidases also may be used in enzymatic bleaching applications, e.g., pulp bleaching and stain bleaching (in detergent compositions).

The concentration of the haloperoxidase in the methods of use of the present invention, is preferably in the range of 0.01–50 mg/l, more preferably in the range of 0.1–10 mg/l.

DNA Recombination (Shuffling)

The nucleotide sequence of SEQ ID NO:1 may be used in a DNA recombination (or shuffling) process. The new polynucleotide sequences obtained in such a process may encode new polypeptides having haloperoxidase activity with improved properties, such as improved stability (storage stability, thermostability), improved specific activity, improved pH-optimum, and/or improved tolerance towards specific compounds.

Shuffling between two or more homologous input polynucleotides (starting-point polynucleotides) involves fragmenting the polynucleotides and recombining the fragments, to obtain output polynucleotides (i.e. polynucleotides that have been subjected to a shuffling cycle) wherein a number of nucleotide fragments are exchanged in comparison to the input polynucleotides.

DNA recombination or shuffling may be a (partially) random process in which a library of chimeric genes is generated from two or more starting genes. A number of known formats can be used to carry out this shuffling or recombination process.

The process may involve random fragmentation of parental DNA followed by reassembly by PCR to new full-length genes, e.g. as presented in U.S. Pat. Nos. 5,605,793, 5,811, 238, 5,830,721, 6,117,679. In-vitro recombination of genes may be carried out, e.g. as described in U.S. Pat. No. 6,159,687, WO98/41623, U.S. Pat. Nos. 6,159,688, 5,965, 408, 6,153,510. The recombination process may take place in vivo in a living cell, e.g. as described in WO 97/07205 and WO 98/28416.

The parental DNA may be fragmented by DNA'se I treatment or by restriction endonuclease digests as described by Kikuchi et al (2000a, Gene 236:159–167). Shuffling of two parents may be done by shuffling single stranded parental DNA of the two parents as described in Kikuchi et al (2000b, Gene 243:133–137).

A particular method of shuffling is to follow the methods described in Crameri et al, 1998, Nature, 391: 288–291 and Ness et al. Nature Biotechnology 17: 893–896. Another format would be the methods described in U.S. Pat. No. 6,159,687: Examples 1 and 2.

The present invention is further described by the following examples, which should not be construed as limiting the scope of the invention.

EXAMPLES

Chemicals used as buffers and substrates were commercial products of at least reagent grade.

Haloperoxidase Assays

Microtiter assays are performed by mixing 100 $\mu$l of haloperoxidase sample (about 0.2 $\mu$g/ml) and 100 $\mu$l assay buffer (0.3 M sodium phosphate; pH 7; 1.25 mM $Na_3VO_4$; 50 mM KBr; 0.008% phenol red). Reactions were initiated by adding 10 $\mu$l of 0.3% $H_2O_2$, and the absorption at 595 nm was measured spectrophotometrically as a function of time in a Molecular Devices Kinetic Microplate reader.

Assays using monochlorodimedone (Sigma M4632, $\epsilon$=20000 $M^{-1}$ $cm^{-1}$ at 290 nm) as a substrate are performed as described below. The decrease in absorption at 290 nm is measured as a function of time. Assays are performed in 0.1 M sodium phosphate or 0.1 M sodium acetate, 50 µM monochlorodimedone, 10 mM KBr/KCl, and 1 mM $H_2O_2$ using a haloperoxidase concentration of about 1 µg/ml. One HU is defined as 1 micromol of monochlorodimedone chlorinated or brominated per minute at pH 5 and 30° C.

Example 1
Transformation and Fermentation of *Aspergillus oryzae*

Protoplast preparation and transformation in *Aspergillus oryzae* of the nucleic acid sequence encoding the *Phaeotrichoconis crotalariae* haloperoxidase contained in the plasmid contained in *E. coli* DH10B, deposited as DSM 13441, was done essentially as described by Christensen et al. (1988), *Biotechnology,* 6:1419–1422. Transformants were plated on AMDS agar plates selecting for the ability to grow on acetamide as sole nitrogen source.

*A. oryzae* transformants were spore purified twice and inoculated into 100 μl YP growth medium supplemented with maltose (3%), 1 mM $Na_3VO_4$, and 0.4% Urea. Cultures were grown at 34° C. for 5 days after which they were assayed for haloperoxidase activity. The best haloperoxidase producer from the transformation was inoculated into 8×125 ml baffled flasks containing YP growth medium with maltose (3%), 1 mM $Na_3VO_4$, and 0.4% Urea and grown for 7 days at 34° C., with shaking at 200 rpm.

Example 2

Purification of *Phaeotrichoconis crotalariae* Haloperoxidase

Glucanex™ (available from Novozymes A/S) treated fermentation broth was centrifuged and the supernatant was filtered through a Seitz EKS filter plate (Seitz-Filter-Werke GmbH, Germany) and concentrated and washed by ultrafiltration on a Filtron Minisette™ system (Filtron Technology Corporation, Massachusetts, USA) with an Omega type membrane (Mw cut-off of 10 kDa) to a final volume of 300 ml and a conductance less than 2 mS.

The crude enzyme preparation was filtered on a glass filter, added 6 ml of a 10 mM sodium orthovanadate, and applied onto an anion exchange column (Pharmacia 26/10 with Q-Sepharose High Performance) equilibrated with 50 mM Tris/HCl pH 7. The column was washed with equilibration buffer and eluted with a 0–1M sodium chloride gradient (over 10 column volumes) in the same buffer using a flow of 10 ml/minute. Fractions of 10 ml were collected and tested for haloperoxidase activity.

Fractions showing haloperoxidase activity were pooled, concentrated by ultrafiltration on an Amicon cell (membrane Mw cut-off of 10 kDa) to a final volume of 15 ml. The concentrated sample was applied onto a 8 ml Source-Q column (Pharmacia) equilibrated with 20 mM Tris/HCl pH 8.0. The column was washed with equilibration buffer and eluted with a 0–1M sodium chloride gradient (over 40 column volumes) in the same buffer using a flow of 3 ml/minute. Fractions of 5 ml were collected and tested for haloperoxidase activity.

Again, fractions showing haloperoxidase activity were pooled, concentrated by ultrafiltration on an Amicon cell (membrane Mw cut-off of 10 kDa) to a final volume of 4.75 ml. Two times 2 ml of the concentrated sample was applied onto a gel filtration column (Pharmacia HiLoad 16/60, Superdex 200High Performance) equilibrated with 50 mM sodium acetate, 100 mM NaCl pH 5.5. The column was eluted with a flow of 1 ml/minute and fractions of 1 ml were collected. Fractions from both runs showing haloperoxidase activity were pooled giving 33 ml with A280=4.718. The pooled fractions contained rather pure haloperoxidase showing only one band on SDS-PAGE with a Mr close to 65 kDa.

Example 3

Thermal Stability of Recombinant *Phaeotrichoconis crotalariae* Haloperoxidase

The thermal stability of *Phaeotrichoconis crotalariae* haloperoxidase was by the following procedure:

The enzyme was diluted to an absorbance at 280 nm of approx. 0.1 in a 0.3 M Tris/HCl buffer pH 7. 0.5 ml portions of the dilution was incubated at 30, 40, 50, 60, 70, and 80° C., respectively, for 15 minutes and then placed on ice-water. A reference sample of the diluted enzyme was kept at 4° C. Activity of the samples was measured according to the phenol red assay in microwell plate using bromide as substrate, and residual activity was calculated relatively to the reference (stored at 4° C.).

Conclusion:

The residual activity of *Phaeotrichoconis crotalariae* haloperoxidase is at least 40% after 15 minutes incubation at 80° C.

TABLE 1

| Temperature (° C.) | Residual activity (%) |
|---|---|
| 4 | 100 |
| 30 | 101.6 |
| 40 | 97.3 |
| 50 | 91.7 |
| 60 | 87.1 |
| 70 | 70.5 |
| 80 | 45.3 |

Example 4

Antibacterial Activity of *Phaeotrichoconis crotalaria* Haloperoxidase against *Escherichia coli*

The antibacterial activity of the *Phaeotrichoconis crotalaria* haloperoxidase, available from Novozymes A/S, DK-2880 Bagsvaerd, Denmark, was tested with bromide as enhancing agent.

The antibacterial activity of haloperoxidase was tested in HEPES-buffer (N-[2-hydroxyethyl]piperazine-N'-[2-ethanesulfonic acid]) (pH 7.0) against *Escherichia coli* DSM 1576 with potassium bromide as electron donor, and hydrogen peroxide was added as electron acceptor. The cells (approximately $10^6$ CFU/ml) were incubated with enzyme for 15 min at 40° C.

The bactericidal activity was determined by incubation in a Malthus Flexi M2060 instrument (available from Malthus Instruments Limited, England). The detection times measured by the Malthus instrument were converted to CFU/ml (colony forming units pr. ml) by a calibration curve. Direct measurements were used when enumerating total survival cells. By the direct measurements, the cell metabolism was determined by conductance measurements in the growth substrate. When the conductance change is measurable by the Malthus instrument, a detection time (dt) will be recorded. The dt's were converted to colony counts by use of a calibration curve relating CFU/ml to dt.

TABLE 2

Results:

| KBr (mM) | Enzyme (mg/L) | $H_2O_2$ (mM) | Bactericidal activity (log CFU/ml) (doublets) |
|---|---|---|---|
| 0 | 0 | 0 | −0.1/0.1 |
| 8 | 0 | 0 | 0.3/0.4 |
| 0 | 0 | 1 | 0.2/0.8 |
| 8 | 0 | 1 | 0.6/0.5 |
| 0 | 1 | 0 | 0.4/0.1 |
| 8 | 1 | 1 | 6.4*/6.4* |

*corresponds to a total kill of the test organism

Bactericidal activity is shown in the table as $\log_{10}$ reduction in the number of living cells (colony forming units), thus a bactericidal activity of 6 correspond to a kill of $10^6$ CFU/ml. A significant bactericidal activity was obtained with the *Phaeotrichoconis crotalaria* haloperoxidase, and no significant bactericidal activity was obtained with any of the controls.

Deposit of Biological Material

An *E. coli* DH10B clone containing a haloperoxidase gene from *Phaeotrichoconis crotalaria* (SEQ ID NO:1) inserted into a pUC19 derived plasmid has been deposited under the terms of the Budapest Treaty with the Deutsche Sammlung von Mikroorganismen und Zelikulturen GmbH (DSMZ), Mascheroder Weg 1b, D-38124 Braunschweig, Germany, and given the following accession number:

| Deposit | Accession Number | Date of Deposit |
|---|---|---|
| NN049532 | DSM 13441 | 2000-Apr-12 |

The deposit was made by Novo Nordisk A/S and was later assigned to Novozymes A/S. The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having haloperoxidase activity, selected from the group consisting of:
   a) a polypeptide having an amino acid sequence which has at least 95% homology with the amino acid sequence of SEQ ID NO:2;
   b) a polypeptide which is encoded by a nucleic acid sequence which hybridizes under medium stringency conditions with (i) the nucleotide sequence of SEQ ID NO:1, (ii) a subsequence of (i) of at least 100 contiguous nucleotides, or (iii) a complementary strand of (i) or (ii);
   c) a fragment of (a) or (b) that has haloperoxidase activity; and
   d) a polypeptide of (a) or (b) having more than 50% residual activity after 15 minutes incubation at 70° C. and pH 7.

2. The polypeptide of claim 1, having an amino acid sequence which has at least 97% homology with the amino acid sequence of SEQ ID NO:2.

3. The polypeptide of claim 1, comprising the amino acid sequence of SEQ ID NO:2.

4. The polypeptide of claim 1, consisting of the amino acid sequence of SEQ ID NO:2 or an enzymatically active fragment thereof.

5. The polypeptide of claim 4, consisting of the amino acid sequence of SEQ ID NO:2.

6. The polypeptide of claim 1, which is encoded by the nucleic acid sequence contained in the plasmid contained in E. coli DH10B, deposited as DSM 13441.

7. A method for producing the polypeptide of claim 1, comprising (a) cultivating a strain to produce a supernatant comprising the polypeptide; and (b) recovering the polypeptide.

8. A method for oxidizing a halide ion comprising reacting the halide ion and a source of hydrogen peroxide in the presence of the polypeptide of claim 1.

9. A method of halogenating a compound, comprising reacting the compound, a halide ion, and a source of hydrogen peroxide in the presence of the polypeptide of claim 1.

10. A method for killing microbial cells or inhibiting growth of microbial cells, comprising contacting the cells with the polypeptide of claim 1, a source of hydrogen peroxide, and a source of halide or thiocyanate in an aqueous solution.

11. A detergent composition, comprising a surfactant and the polypeptide of claim 1.

* * * * *

SEQUENCE LISTING

```
<160> NUMBER OF SEQ ID NOS: 2

<210> SEQ ID NO 1
<211> LENGTH: 1797
<212> TYPE: DNA
<213> ORGANISM: Phaeotrichoconis crotalariae
<220> FEATURE:
<221> NAME/KEY: CDS
<222> LOCATION: (1)..(1797)

<400> SEQUENCE: 1 atg act tcg gtt aca ccc att ccg ctc cct aca atc gac gaa cct gaa      48
Met Thr Ser Val Thr Pro Ile Pro Leu Pro Thr Ile Asp Glu Pro Glu
1               5                   10                  15 gag tac aac acc aac tac ata ctc tac tgg aac cat gtc ggt tta caa      96
Glu Tyr Asn Thr Asn Tyr Ile Leu Tyr Trp Asn His Val Gly Leu Gln
            20                  25                  30 ctc aac cgc gta aca cac act gtc ggg gga ccc ctg acg gga cca ccc     144
Leu Asn Arg Val Thr His Thr Val Gly Gly Pro Leu Thr Gly Pro Pro
        35                  40                  45 ctc tct gcc aga gct ctg ggc atg ctg cac ttg gct atc cac gac gcc     192
Leu Ser Ala Arg Ala Leu Gly Met Leu His Leu Ala Ile His Asp Ala
    50                  55                  60 tac ttt tct atc tac cct tcg gct gat ttt tcg acc ttt ctc tct cct     240
Tyr Phe Ser Ile Tyr Pro Ser Ala Asp Phe Ser Thr Phe Leu Ser Pro
65                  70                  75                  80
```

-continued

| | |
|---|---|
| gat gct gag aat gcc gcg tac cgt ctt ccc agc ccc aat ggt gca gac<br>Asp Ala Glu Asn Ala Ala Tyr Arg Leu Pro Ser Pro Asn Gly Ala Asp<br>85                         90                   95 | 288 |
| gat gct cgt caa gca gtc gct gga gcg tca ctc aaa atg ctg tct tca<br>Asp Ala Arg Gln Ala Val Ala Gly Ala Ser Leu Lys Met Leu Ser Ser<br>100                      105                  110 | 336 |
| ttg tat atg agg cct gag gcc ccc agc ccc aac atc tcc gac aac gcg<br>Leu Tyr Met Arg Pro Glu Ala Pro Ser Pro Asn Ile Ser Asp Asn Ala<br>115                      120                  125 | 384 |
| tat gcc cag ctt caa ctg att ctt gac caa tca gct gtg gaa gcg cct<br>Tyr Ala Gln Leu Gln Leu Ile Leu Asp Gln Ser Ala Val Glu Ala Pro<br>130                      135                  140 | 432 |
| ggc ggt gtt gac cgt gct tca gcc agt ttc ttg ttt ggt gag gct gta<br>Gly Gly Val Asp Arg Ala Ser Ala Ser Phe Leu Phe Gly Glu Ala Val<br>145                      150                  155                  160 | 480 |
| gcg gat gtc ttc ttc gca ctc ctc aac gat ccg cga ggc gct tcg cag<br>Ala Asp Val Phe Phe Ala Leu Leu Asn Asp Pro Arg Gly Ala Ser Gln<br>165                      170                  175 | 528 |
| gag ggc tac cac cct acg cct ggc cgc tac aaa ttc gac gac gaa cct<br>Glu Gly Tyr His Pro Thr Pro Gly Arg Tyr Lys Phe Asp Asp Glu Pro<br>180                      185                  190 | 576 |
| act cat cct gtc gtc cta att cca gta gat ccc aac aac cct agt ggt<br>Thr His Pro Val Val Leu Ile Pro Val Asp Pro Asn Asn Pro Ser Gly<br>195                      200                  205 | 624 |
| ccc aag aag cca ttc cgt cag tac cat gcc ccg ttc tac ggc aag act<br>Pro Lys Lys Pro Phe Arg Gln Tyr His Ala Pro Phe Tyr Gly Lys Thr<br>210                      215                  220 | 672 |
| acg aag cgt ttc gcc acg cag aca gag cat gtg ctc gcc gac cca ccg<br>Thr Lys Arg Phe Ala Thr Gln Thr Glu His Val Leu Ala Asp Pro Pro<br>225                      230                  235                  240 | 720 |
| ggc ctg cgt tct aat gcg gac gag act gcc gag tat gac gac tcc atc<br>Gly Leu Arg Ser Asn Ala Asp Glu Thr Ala Glu Tyr Asp Asp Ser Ile<br>                      245                  250                  255 | 768 |
| cgc gtc gct att gcc atg gga ggc gcc act gat ctc aac tcc acc aag<br>Arg Val Ala Ile Ala Met Gly Gly Ala Thr Asp Leu Asn Ser Thr Lys<br>           260                  265                  270 | 816 |
| cgc agc cca tgg cag aca gca cag ggc ctg ttc tgg gcc tac gat ggg<br>Arg Ser Pro Trp Gln Thr Ala Gln Gly Leu Phe Trp Ala Tyr Asp Gly<br>275                      280                  285 | 864 |
| tca aac ctt gtt ggc aca cca cct cgt ttt tac aac caa att gtg cgt<br>Ser Asn Leu Val Gly Thr Pro Pro Arg Phe Tyr Asn Gln Ile Val Arg<br>290                      295                  300 | 912 |
| cgc atc gca gtg acg tac aag aaa gag gag gac cta gca aac agc gaa<br>Arg Ile Ala Val Thr Tyr Lys Lys Glu Glu Asp Leu Ala Asn Ser Glu<br>305                      310                  315                  320 | 960 |
| gtc aac aac gcg gac ttc gca cgc ctc ttc gcc ctc gtc gac gtc gct<br>Val Asn Asn Ala Asp Phe Ala Arg Leu Phe Ala Leu Val Asp Val Ala<br>                      325                  330                  335 | 1008 |
| tgc acg gac gcc ggt atc ttc tcc tgg aaa gaa aaa tgg gag ttt gaa<br>Cys Thr Asp Ala Gly Ile Phe Ser Trp Lys Glu Lys Trp Glu Phe Glu<br>                      340                  345                  350 | 1056 |
| ttc tgg cgc cca ctc tcc ggc gta cgg gat gac ggc cgt cca gac cac<br>Phe Trp Arg Pro Leu Ser Gly Val Arg Asp Asp Gly Arg Pro Asp His<br>355                      360                  365 | 1104 |
| ggc gac ccc ttc tgg ctc acc ctc ggc gct cct gcc aca aac aca aac<br>Gly Asp Pro Phe Trp Leu Thr Leu Gly Ala Pro Ala Thr Asn Thr Asn<br>370                      375                  380 | 1152 |
| gac atc ccc ttc aag ccc ccc ttc ccc gcc tac ccg tcc ggc cac gcg<br>Asp Ile Pro Phe Lys Pro Pro Phe Pro Ala Tyr Pro Ser Gly His Ala | 1200 |

```
                385                 390                 395                 400
acc ttt ggc ggc gcc gtc ttc caa atg gtg cgc cgc tac tac aac ggg              1248
Thr Phe Gly Gly Ala Val Phe Gln Met Val Arg Arg Tyr Tyr Asn Gly
                    405                 410                 415 cgc gtc ggc acg tgg aag gac aac gag ccc gac aac atc gcc atc gac              1296
Arg Val Gly Thr Trp Lys Asp Asn Glu Pro Asp Asn Ile Ala Ile Asp
            420                 425                 430 atg gtc atc tct gag gag ctc aac ggc ctc agc cgc gac ctc cgc cag              1344
Met Val Ile Ser Glu Glu Leu Asn Gly Leu Ser Arg Asp Leu Arg Gln
                435                 440                 445 ccc tac gat ccc act gcc ccg atc caa gac caa ccg ggt atc gtg cgc              1392
Pro Tyr Asp Pro Thr Ala Pro Ile Gln Asp Gln Pro Gly Ile Val Arg
            450                 455                 460 acc cgc atc gtg cgc cac ttt agc tcc gcg tgg gaa atg atg ttt gaa              1440
Thr Arg Ile Val Arg His Phe Ser Ser Ala Trp Glu Met Met Phe Glu
465                 470                 475                 480 aac gcc att tct cgc atc ttc ctc ggc gtc cac tgg cgc ttc gat gcc              1488
Asn Ala Ile Ser Arg Ile Phe Leu Gly Val His Trp Arg Phe Asp Ala
                485                 490                 495 gcc gcc gcg cgc gac att ctt atc ccc act acc aca aaa gac gtc tat              1536
Ala Ala Ala Arg Asp Ile Leu Ile Pro Thr Thr Thr Lys Asp Val Tyr
            500                 505                 510 gct gtt gat gcc aat ggc gcg acg gtg ttc cag aat gtc gag gat gtc              1584
Ala Val Asp Ala Asn Gly Ala Thr Val Phe Gln Asn Val Glu Asp Val
        515                 520                 525 agg tat gag acc aag ggg acc cgt gag ggc tgt gag ggc ctg tat ccg              1632
Arg Tyr Glu Thr Lys Gly Thr Arg Glu Gly Cys Glu Gly Leu Tyr Pro
    530                 535                 540 att ggg ggc gtg ccg ctg ggg att gag att gcg aat gag att ttt gag              1680
Ile Gly Gly Val Pro Leu Gly Ile Glu Ile Ala Asn Glu Ile Phe Glu
545                 550                 555                 560 agt ggg ttg agg cct acg ccc ccg gag agg cag ccg atg ccg cag gac              1728
Ser Gly Leu Arg Pro Thr Pro Pro Glu Arg Gln Pro Met Pro Gln Asp
                565                 570                 575 acg ccg gag cag aag ggg gtg aag ggg atg tgg gag gag gag cag gcg              1776
Thr Pro Glu Gln Lys Gly Val Lys Gly Met Trp Glu Glu Glu Gln Ala
            580                 585                 590 ccg ctg gtg agg gag gcg ccg                                                  1797
Pro Leu Val Arg Glu Ala Pro
        595

<210> SEQ ID NO 2
<211> LENGTH: 599
<212> TYPE: PRT
<213> ORGANISM: Phaeotrichoconis crotalariae

<400> SEQUENCE: 2

Met Thr Ser Val Thr Pro Ile Pro Leu Pro Thr Ile Asp Glu Pro Glu
1               5                   10                  15

Glu Tyr Asn Thr Asn Tyr Ile Leu Tyr Trp Asn His Val Gly Leu Gln
            20                  25                  30

Leu Asn Arg Val Thr His Thr Val Gly Gly Pro Leu Thr Gly Pro Pro
        35                  40                  45

Leu Ser Ala Arg Ala Leu Gly Met Leu His Leu Ala Ile His Asp Ala
    50                  55                  60

Tyr Phe Ser Ile Tyr Pro Ser Ala Asp Phe Ser Thr Phe Leu Ser Pro
65                  70                  75                  80

Asp Ala Glu Asn Ala Ala Tyr Arg Leu Pro Ser Pro Asn Gly Ala Asp
                85                  90                  95
```

```
Asp Ala Arg Gln Ala Val Ala Gly Ala Ser Leu Lys Met Leu Ser Ser
                100                 105                 110

Leu Tyr Met Arg Pro Glu Ala Pro Ser Pro Asn Ile Ser Asp Asn Ala
            115                 120                 125

Tyr Ala Gln Leu Gln Leu Ile Leu Asp Gln Ser Ala Val Glu Ala Pro
        130                 135                 140

Gly Gly Val Asp Arg Ala Ser Ala Ser Phe Leu Phe Gly Glu Ala Val
145                 150                 155                 160

Ala Asp Val Phe Phe Ala Leu Leu Asn Asp Pro Arg Gly Ala Ser Gln
                165                 170                 175

Glu Gly Tyr His Pro Thr Pro Gly Arg Tyr Lys Phe Asp Asp Glu Pro
            180                 185                 190

Thr His Pro Val Val Leu Ile Pro Val Asp Pro Asn Asn Pro Ser Gly
        195                 200                 205

Pro Lys Lys Pro Phe Arg Gln Tyr His Ala Pro Phe Tyr Gly Lys Thr
        210                 215                 220

Thr Lys Arg Phe Ala Thr Gln Thr Glu His Val Leu Ala Asp Pro Pro
225                 230                 235                 240

Gly Leu Arg Ser Asn Ala Asp Glu Thr Ala Glu Tyr Asp Asp Ser Ile
                245                 250                 255

Arg Val Ala Ile Ala Met Gly Gly Ala Thr Asp Leu Asn Ser Thr Lys
                260                 265                 270

Arg Ser Pro Trp Gln Thr Ala Gln Gly Leu Phe Trp Ala Tyr Asp Gly
            275                 280                 285

Ser Asn Leu Val Gly Thr Pro Pro Arg Phe Tyr Asn Gln Ile Val Arg
        290                 295                 300

Arg Ile Ala Val Thr Tyr Lys Lys Glu Glu Asp Leu Ala Asn Ser Glu
305                 310                 315                 320

Val Asn Asn Ala Asp Phe Ala Arg Leu Phe Ala Leu Val Asp Val Ala
                325                 330                 335

Cys Thr Asp Ala Gly Ile Phe Ser Trp Lys Glu Lys Trp Glu Phe Glu
            340                 345                 350

Phe Trp Arg Pro Leu Ser Gly Val Arg Asp Asp Gly Arg Pro Asp His
        355                 360                 365

Gly Asp Pro Phe Trp Leu Thr Leu Gly Ala Pro Ala Thr Asn Thr Asn
370                 375                 380

Asp Ile Pro Phe Lys Pro Pro Phe Pro Ala Tyr Pro Ser Gly His Ala
385                 390                 395                 400

Thr Phe Gly Gly Ala Val Phe Gln Met Val Arg Arg Tyr Tyr Asn Gly
                405                 410                 415

Arg Val Gly Thr Trp Lys Asp Asn Glu Pro Asp Asn Ile Ala Ile Asp
            420                 425                 430

Met Val Ile Ser Glu Glu Leu Asn Gly Leu Ser Arg Asp Leu Arg Gln
        435                 440                 445

Pro Tyr Asp Pro Thr Ala Pro Ile Gln Asp Gln Pro Gly Ile Val Arg
        450                 455                 460

Thr Arg Ile Val Arg His Phe Ser Ser Ala Trp Glu Met Met Phe Glu
465                 470                 475                 480

Asn Ala Ile Ser Arg Ile Phe Leu Gly Val His Trp Arg Phe Asp Ala
                485                 490                 495

Ala Ala Ala Arg Asp Ile Leu Ile Pro Thr Thr Thr Lys Asp Val Tyr
            500                 505                 510
```

```
Ala Val Asp Ala Asn Gly Ala Thr Val Phe Gln Asn Val Glu Asp Val
        515                 520                 525

Arg Tyr Glu Thr Lys Gly Thr Arg Glu Gly Cys Glu Gly Leu Tyr Pro
        530                 535                 540

Ile Gly Gly Val Pro Leu Gly Ile Glu Ile Ala Asn Glu Ile Phe Glu
545                 550                 555                 560

Ser Gly Leu Arg Pro Thr Pro Pro Glu Arg Gln Pro Met Pro Gln Asp
                565                 570                 575

Thr Pro Glu Gln Lys Gly Val Lys Gly Met Trp Glu Glu Glu Gln Ala
            580                 585                 590

Pro Leu Val Arg Glu Ala Pro
            595
```